United States Patent [19]

Berke

[11] Patent Number: 5,165,400

[45] Date of Patent: Nov. 24, 1992

[54] CONVECTIVE HYPERTHERMIA ARTICLE

[75] Inventor: Leonard D. Berke, Cincinnati, Ohio

[73] Assignee: Cincinnati Sub-Zero Products, Inc., Cincinnati, Ohio

[21] Appl. No.: 663,555

[22] Filed: Mar. 4, 1991

[51] Int. Cl.$^5$ ................................................ A61F 7/00
[52] U.S. Cl. ...................................... 128/400; 5/482
[58] Field of Search ............... 128/379, 402, 400, 309,
128/376, 380; 5/482, 485; 219/212; 165/46;
62/259.3

[56] References Cited

U.S. PATENT DOCUMENTS

| | | | |
|---|---|---|---|
| 1,004,192 | 9/1911 | Phelan | 128/400 |
| 2,110,022 | 3/1938 | Kliesrath | 5/334 |
| 2,601,189 | 6/1952 | Wales | 5/482 |
| 3,757,366 | 9/1973 | Sacher | 128/400 |
| 4,572,188 | 2/1986 | Augustine et al. | 128/380 |
| 4,660,388 | 4/1987 | Greene | 5/485 |
| 4,777,802 | 10/1988 | Feher | 5/482 |
| 4,867,230 | 9/1989 | Voss | 128/402 |

Primary Examiner—Mark Graham
Attorney, Agent, or Firm—Charles R. Wilson

[57] ABSTRACT

A convective hyperthermia article is disclosed. The article has a generally U-shaped hollow body with two legs and a cross piece connecting the legs. The article is dimensioned to lie adjacent a patient's body and extend a substantial length thereof. A set of air holes is spaced on at least the underside of the article. The article also has a receptacle opening to detachably receive an air hose from a heat source. Heated air is received in the interior of the hyperthermia article and directed through the air holes onto the patient's body. The article is economically produced so as to be disposable.

16 Claims, 3 Drawing Sheets

CONVECTIVE HYPERTHERMIA ARTICLE

This invention relates to a hyperthermia article. More particularly, the invention relates to a disposable hyperthermia article for use with a heat source to supply a source of controlled temperature air to a patient's body surface.

Hypothermia is a condition experienced by warm blooded animals after some abnormal event. An individual who has had prolonged exposure to a hostile environment such as freezing rain, snow, bitter cold, etc. can experience shivering and eventually hypothermia. In fact, body temperature can drop to a point where it is life threatening. A person who has just undergone an operation is also prone to experience hypothermia. Influencing factors for hypothermia in these patients include the loss of body heat due to body exposure during pre-operation prepping, cold operating room temperatures, breathing of dry anesthetic gases, adverse effects of anesthesia on body heat production and inhibition of body temperature regulation, evaporation of moisture from exposed organs during the operation and cold intravenous fluids.

Regardless of the cause of hypothermia, the individual initially experiences extreme discomfort. The discomfort can quickly lead to a life threatening situation. Anyone suffering from hypothermia should be attended to so as to avoid irreversible body temperature drop or even death. An obvious cure to the problem is to raise the body temperature of the individual. Simply wrapping a person suffering from hypothermia in a blanket is an obvious solution which can provide some relief. The effect of the blanket is to retain body heat. This does result in a gradual warming of the body. However, there are times when a blanket alone will not suffice. The ability of the body to produce sufficient heat in sufficient time may not be possible or feasible in certain situations. Additionally, use of a blanket after an operation in a hospital can be cumbersome. It may be difficult to fully cover the patient's body due to intravenous tubing and other life supporting equipment which physically hinders placement of the blanket.

Various articles have been developed for use specifically on victims suffering from hypothermia. Such articles are specially constructed for use by professionally trained individuals. Specially constructed blankets are capable of having a fluid circulating through tubes embedded in the blanket. The temperature of the fluid in the blanket is controlled by an external source. In effect, the blanket not only retains the heat of the individual but supplies heat to the patient.

There also have been devised various articles which control the patient's body temperature by directing temperature controlled air to the surface of the body. Thus, there are articles which are dimensioned to overlie the patient's body much as a blanket does. Air is directed into the article and through holes in the article so as to contact the body. For instance, U.S. Pat. No. 2,110,022 discloses a flexible bag which has an insulated top layer and a heat conducting bottom layer. The bottom layer contacts the patient. Air is circulated inside the bag with a portion of the air escaping through ports. The bag is such that the top and sides can be manipulated so as to press against the patient thereby blocking exit ports and reducing the area of the body over which the air circulates. U.S. Pat. No. 4,572,188 also discloses a cover type blanket of inflatable casing. The cover has a plurality of elongated inflatable tubes with upper and lower surfaces. An entry port in the upper surface permits thermally controlled warmed air to flow into the main tube of the casing and then through other ports into other adjoining tubes. The cover is inflated in this manner. Exit ports are found in the lower surface of the cover to permit the thermally controlled air to blow out of the exit ports and onto the patient. An external heat source is used to supply the warm air.

The problems of hypothermia are experienced widely by both emergency rescue units and hospital personnel. Various attempts have been made to treat victims suffering from the condition. However, there is still a need for an improved product. Products of the prior art are deficient in one or more ways; for example, heat retention effectiveness, cost of construction, strength of materials, bulkiness, weight and ease of use.

There has now been developed a convective hyperthermia article primarily for use by hospital personnel to treat patients. The hyperthermia article is constructed in a manner which effectively provides heated air to the patient's body surface. The construction of the article is such that it is economical to produce, easy to use and provides various features deemed necessary or desirable by medical professionals.

SUMMARY OF THE INVENTION

A light weight disposable convective hyperthermia article is disclosed for use in controlling a patient's body temperature. The article has a generally U-shaped hollow body comprised of two legs and a cross piece connecting the legs. The article is dimensioned to lie in close proximity to the patient's body and extend a substantial length thereof. The article has a receptacle opening to detachably receive an air hose from a heat generating unit. Heated air is received into the interior of the U-shaped hollow body. A set of substantially uniformly spaced air holes along the two legs and cross piece are used for directing the heated air from the interior of the article to the patient's body surface.

DETAILED DESCRIPTION OF THE INVENTION

The convective hyperthermia article of this invention is described in detail in the following paragraphs. While the article is described with particular reference to the drawings, it should be understood that other variations of the invention are possible.

Figure 1:
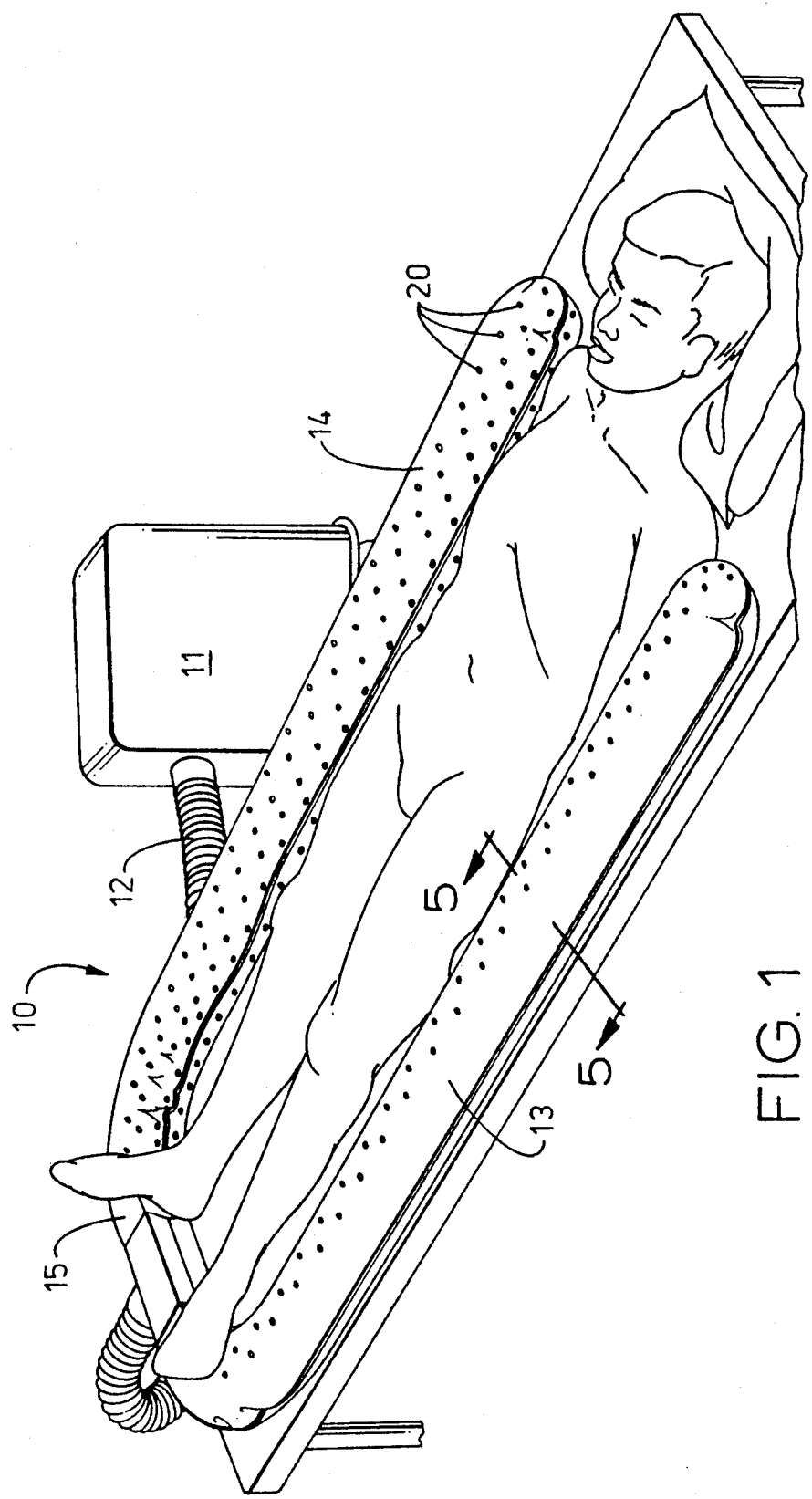
FIG. 1 is a schematic view in perspective of the convective hyperthermia article of this invention positioned for use.
Figure 2:
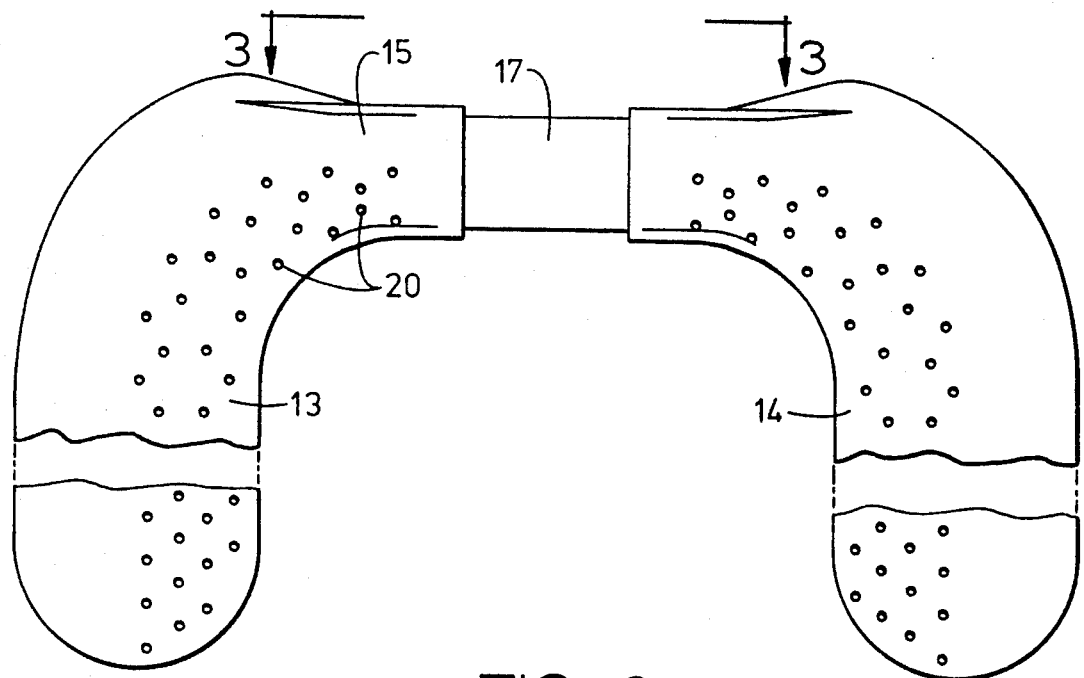
FIG. 2 is a plan view of the hyperthermia article of FIG. 1.

With reference to FIG. 1, there is shown a convective hyperthermia article 10 positioned partially around a patient. The article 10 is operably connected to a heat source 11 by means of an air delivery hose 12. The heat source 11 is a conventional electric resistance heater with thermostat controls to supply a source of heated air to an outlet. A fan built into the heat source forces the heated air through the outlet and into the delivery hose 12. Heat sources of this general nature are well known and are commercially available. Most are electric resistance heaters with sensitive thermostat means to control the temperature of the air. Various monitoring means and safety shut-off means are typically built into such heat sources especially when contemplated for use by medical personnel.

The convective hyperthermia article 10 has a generally U-shaped hollow body comprised of hollow legs 13 and 14 and a hollow cross piece 15 connecting the legs. The U-shaped body is dimensioned to lie in close proximity to a patient's body and is intended to extend from foot to neck and from side to side. Preferably, the article is dimensioned to lie adjacent the outline of a patient's body such that direct contact with the patient is not made. For an adult patient, the legs of the article range from about four feet to about six feet in length and the cross piece ranges from about two feet to about three feet in length. The cross dimension of the legs and cross piece is not critical, though typically ranges from about three inches to about eight inches. The legs and cross piece are flexible to allow folding the article during shipping and storage and most importantly during use. Thus, the length of the legs can be shortened to accommodate the particular patient simply by folding the legs upon themselves prior to or after forcing heated air into them.

Suitable materials used in construction of the article include woven and non-woven fabrics and cellulosics. A particularly preferred material is a non-woven fabric having a thin plastic coating covering at least one side. The material is water-proof and air impervious.

Figure 3:
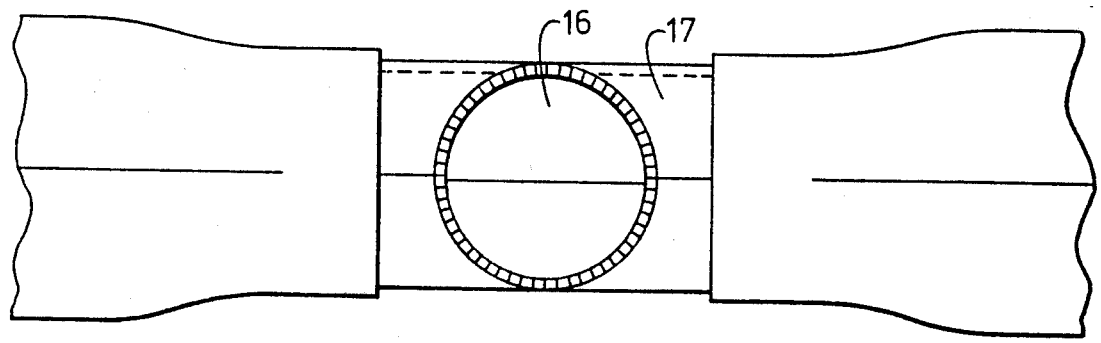
FIG. 3 is an end view of the hyperthermia article of FIG. 1 showing a receptacle opening for receiving an air hose.
Figure 4:
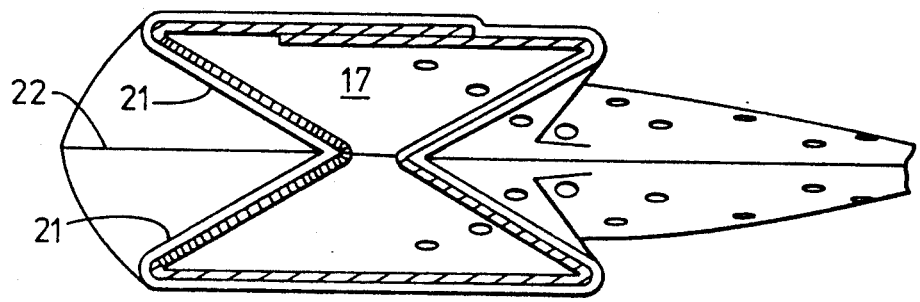
FIG. 4 is a partial sectional view of a reinforcing collar found on the hyperthermia article of FIG. 1.
Figure 5:
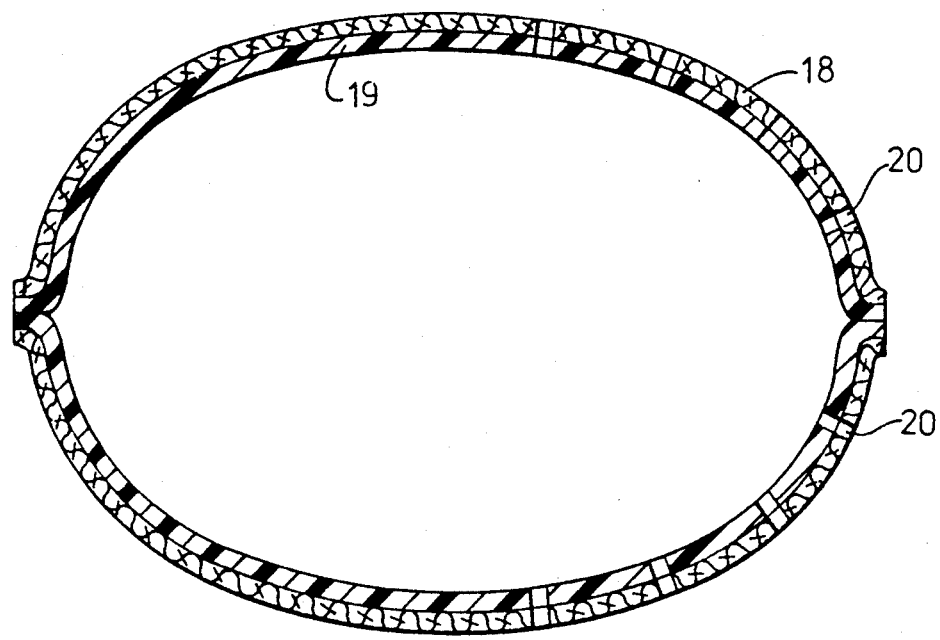
FIG. 5 is a partial sectional view of the U-shaped hollow body of the hyperthermia article of FIG. 1.

A receptacle opening 16 is positioned in the approximate center side wall of the cross piece 15 for the purpose of receiving the air delivery hose 12 from the heat source 11. It can as well be positioned elsewhere along the article, e.g. in a top wall of the cross piece or in the end of one of the legs. The opening is shaped to match the end portion of the air delivery hose in a sealing fashion. A semi-rigid reinforcing collar 17 is interposed in the cross piece and surrounds the opening to better hold and retain the hose. As best seen in FIGS. 3 and 4, the collar 17 extends the circumference of the cross piece 15. The collar preferably has a collapsible design which allows it to fold down upon itself. This feature allows the collar to flatten and the article to be readily folded and packaged in a compact container. Thus, the collar 17 has fold lines 21 extending diagonally from outer peripheries to a center line 22 which facilitate the collapsing of the collar. It has been found the collar 17 is able to retain the air delivery hose and provides sufficient rigidity that air blown through the hose into the opening will impinge upon the collar opposite the opening and be substantially evenly directed to each leg. The semi-rigid nature of the collar ensures that the flexible walls of the article will not collapse or partially fold at the receptacle opening area to impede the flow of air to each leg.

A set of substantially uniformly spaced air holes 20 is provided in at least the inner area of the legs and cross piece. The air holes can be punched into the article throughout its entire surface area for maximum air flow, though optimum air flow directed to the patient is achieved when the holes are provided in the inside approximate half of the article's U-shaped body. The holes can extend through only a bottom side of the article so that the heated air received from the heat source unit is directed onto a patient's body. However, for manufacturing reasons, the holes extend through both the top and bottom sides of the article. The diameter of each hole is generally in the range of about 30 mils to about 250 mils. A hole density of about one hole to about five holes per square inch of surface area is sufficient, though a greater or lesser number can be utilized depending on hole diameter and air flow-rate of the contemplated heat source.

In operation, the convective hyperthermia article is initially positioned adjacent a patient who is shivering or otherwise shows symptoms of hypothermia. The cross piece of the article is placed around the patient's feet with the legs extending substantially along the patient's body to near his head. If needed, the ends of each leg of the article are folded over so as to effectively shorten the overall length. Next, the air delivery hose is inserted into the article's receptacle opening. The temperature control of the heat source is set to a desired setting and the heat source activated. Heated air flows through the delivery hose and into the hyperthermia article. The article is eventually filled with the heated air, whereupon it then passes through the air openings and unto the patient. A sheet or blanket is normally placed over the convective hyperthermia article to help retain the heated air proximate to the patient. When the patient's body temperature returns to normal, the article is removed and discarded.

While the invention has been described in detail with reference to the drawings, it should be understood other variations and modifications are possible. All such changes of an obvious nature are considered within the scope of the following claims.

What is claimed is:

1. A light-weight disposable convective hyperthermia article for use in controlling a patient's body temperature, said article having a generally U-shaped air filled hollow body having an interior and an exterior and comprised of two legs and a cross piece connecting the legs, said article dimensioned and adapted to lie adjacent the patient's body and extend a substantial length thereof and made of a sufficiently flexible material to permit folding into a compact unit for storage and to permit folding and shaping to accommodate the patient, further said article having a receptacle opening to detachably receive an air hose from a heat source for receiving heated air into the interior of the U-shaped body and a set of spaced air holes in the legs and in the cross piece of the U-shaped body adapted for passing the heated air from the interior to proximate the patient.

2. The hyperthermia article of claim 1 wherein the U-shaped hollow body is made of non-woven fabric having a thin plastic coating covering at least one side thereof.

3. The hyperthermia article of claim 1 wherein the receptacle opening is in an approximate center of the cross piece.

4. The hyperthermia article of claim 3 wherein the receptacle opening in the U-shaped body is positioned on an outside side wall of the cross piece.

5. The hyperthermia article of claim 1 further having a semi-rigid reinforcing collar interposed in the cross piece and the receptacle opening being positioned in the collar to better hold and retain the air hose.

6. The hyperthermia article of claim 2 wherein the air holes in the U-shaped hollow body are spaced to provide a hole density of from about one per square inch to about five per square inch.

7. The hyperthermia article of claim 6 wherein the air holes are positioned substantially uniformly in an approximate inside half of the U-shaped hollow body thereby adapted to ensure a flow of heated air to a restricted part of the patient.

8. The hyperthermia article of claim 7 wherein the air holes have a diameter of from about 30 mils to about 250 mils.

9. The hyperthermia article of claim 1 wherein the legs of the U-shaped body are from about four feet to about six feet in length and the cross piece of the U-shaped body is from about two feet to about three feet in length.

10. A light-weight disposable convective hyperthermia article for use in controlling a patient's body temperature, said article having a generally U-shaped hollow body having an interior and an exterior and having two legs and a cross piece connecting the legs, said article dimensioned to lie adjacent the patient's body and extend a substantial length thereof, further said article having a semi-rigid reinforcing collar interposed in the cross piece with a receptacle opening positioned therein to detachably receive an air hose from a heat source for receiving heated air into the interior of the U-shaped body and a set of air holes spaced in the U-shaped hollow body adapted for passing heated air from the interior to proximate the patient.

11. The hyperthermia article of claim 10 wherein the U-shaped hollow body is sufficiently flexible to permit a folding and shaping thereof adapted to accommodate the patient.

12. The hyperthermia article of claim 11 wherein the U-shaped hollow body is made of a non-woven fabric having a thin plastic coating covering at least one side thereof.

13. The hyperthermia article of claim 12 wherein the air holes in the U-shaped hollow body are spaced to provide a hole density of from about one per square inch to about five per square inch.

14. The hyperthermia article of claim 13 wherein the air holes are positioned substantially uniformly in an approximate inside half of the U-shaped hollow body thereby adapted to ensure a flow of heated air towards the patient.

15. The hyperthermia article of claim 14 wherein the air holes have a diameter of from about 30 mils to about 250 mils.

16. The hyperthermia article of claim 10 wherein the legs of the U-shaped body are from about four feet to about six feet in length and the cross piece of the U-shaped body is from about two feet to about three feet in length.

* * * * *